US006184446B1

(12) United States Patent
Walejko

(10) Patent No.: US 6,184,446 B1
(45) Date of Patent: Feb. 6, 2001

(54) INBRED CORN LINE GSC3

(75) Inventor: Ronald Walejko, Livingston, WI (US)

(73) Assignee: Golden Seed Company LLC, Cordova, IL (US)

( * ) Notice: Under 35 U.S.C. 154(b), the term of this patent shall be extended for 0 days.

(21) Appl. No.: 09/378,927

(22) Filed: Aug. 23, 1999

(51) Int. Cl.[7] .............................. A01H 5/00; A01H 4/00; A01H 1/00; C12N 5/00
(52) U.S. Cl. .................. 800/320.1; 800/298; 800/275; 800/271; 800/301; 800/302; 800/303; 435/412; 435/424; 435/430; 435/430.1
(58) Field of Search .................. 800/320.1, 298, 800/295, 278, 275, 271, 301–303; 435/419, 468, 412, 424, 430, 430.1; 536/24.1

Primary Examiner—Gary Benzion
(74) Attorney, Agent, or Firm—Rothwell, Figg, Ernst & Manbeck

(57) ABSTRACT

An inbred corn line, designated GSC3, is disclosed. The invention relates to the seeds of inbred corn line GSC3, to the plants of inbred corn line GSC3 and to methods for producing a corn plant produced by crossing the inbred line GSC3 with itself or another corn line. The invention further relates to hybrid corn seeds and plants produced by crossing the inbred line GSC3 with another corn line.

30 Claims, No Drawings

INBRED CORN LINE GSC3

BACKGROUND OF THE INVENTION

The present invention relates to a new and distinctive corn inbred line, designated GSC3. There are numerous steps in the development of any novel, desirable plant germplasm. The first step is to define and analyze the problems and weaknesses of the current germplasm, establish the program goals, and define the specific breeding objectives. The next step is to select germplasm that possess the traits that meet the program goals. The ultimate goal is to combine in a single variety or hybrid an improved combination of desirable traits from the parental germplasm. These traits may include higher yield, better resistance to diseases and insects, better stalks and roots, increased tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a few locations is effective, whereas, for low heritable traits, selection should be based on mean values obtained from replicated evaluations of families of related plants. Popular selection methods include pedigree selection, modified pedigree selection, mass selection, and recurrent selection.

The complexity of inheritance influences the choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, however, each evaluation should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) a minimum of three years. The best lines are candidates for new commercial cultivars; those still deficient in a few traits are used as parents to produce new populations for further selection.

This process, which leads to the final step of marketing and distribution, usually take from eight to twelve years from the time the first cross is made. Therefore, development of new cultivars is a time-consuming process that requires precise forward planning, efficient use of resources, and minimum changes in direction.

The true genotypic value of most traits is masked by other confounding plant traits and/or environmental factors making it difficult to identify genetically superior individuals. One method of identifying a superior plant is to observe its performance relative to other experimental plants and to a widely grown standard cultivar. If a single observation is inconclusive, replicated observations are made to provide a better estimate of the plant's genetic worth.

The goal of plant breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutating. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The resulting inbred lines are unpredictable. This unpredictability occurs because the breeder's selection is made in unique environments, with no control at the DNA level (using conventional breeding procedures), and different genetic combinations being generated. A breeder of ordinary skill cannot predict the resulting lines except possibly in a very gross and general fashion. The same breeder cannot produce the same line twice even using the exact same original parents and the same selection techniques. This unpredictability results in the expenditure of large research monies to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines; the hybrids from these crosses are evaluated to determine which have commercial potential.

Pedigree breeding is used commonly to improve self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals usually begins in the $F_2$ population; then, in the $F_3$ line, the best individuals in the best families are selected. Replicated tests of families, or hybrid combinations of individuals within these families, often follow in the $F_4$ generation to improve the effectiveness of the selection of low heritable traits. In the advanced stages of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding can be used to transfer genes of a highly heritable trait into a desirable homozygous cultivar or inbred line (the recurrent parent). The source of the transferred trait is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is comparable with industry standards or that creates a new market. The seed producer, grower, processor, and consumer will incur additional costs with the introduction of a new cultivar for special advertising and marketing, altered seed and commercial production practices, and new product utilization. The testing preceding the release of a new cultivar should take into consideration research and development costs as well as technical superiority of the final cultivar. For seed-propagated cultivars, easy and economical seed production must be feasible.

Once the best-performing inbreds have been identified, the hybrid seed can be reproduced indefinitely provided the homogeneity of the inbred parent is maintained. A single-cross hybrid is produced by crossing two inbred lines to produce the $F_1$ progeny (A×B). A double-cross hybrid is produced by crossing two desirable single crosses (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop stable, high yielding, agronomically sound corn hybrids. The reasons for this goal are to maximize the amount of grain produced and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated GSC3. This invention thus relates to the seeds of inbred corn line GSC3, to the plants of inbred corn line GSC3 and to the methods for producing a corn plant by crossing the inbred corn line GSC3 with itself or another corn line. This invention further relates to hybrid corn seeds and plants produced by crossing the inbred line GSC3 with another corn line. The inbred corn plant of the invention may further comprise, or have, a cytoplasmic factor that is capable of conferring male sterility. Parts of the corn plant of the present invention are also provided, such as e.g., pollen obtained from an inbred plant and an ovule of the inbred plant.

In one aspect, the present invention provides for single gene converted plants of GSC3. The single transferred gene may preferably be a dominant or recessive allele. Preferably, the single transferred gene will confer such traits as male sterility, herbicide resistance, insect resistance, resistance for bacterial, fungal, or viral disease, male fertility, enhanced nutritional quality, and industrial usage. The single gene may be a naturally occurring maize gene or a transgene introduced through genetic engineering techniques.

In another aspect, the present invention provides regenerable cells for use in tissue culture or inbred corn plant GSC3. The tissue culture will preferably be capable of regenerating plants having the physiological and morphological characteristics of the foregoing inbred corn plant, and of regenerating plants having substantially the same genotype as the foregoing inbred corn plant. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, the present invention provides corn plants regenerated from the tissue cultures of the invention.

DEFINITIONS

In the following descriptions and tables contain a number of terms. These terms are defined below to provide a clear and consistent understanding of the specification and claims, including the scope to be given such terms:

Yield (Bushels/Acre). The actual yield of the grain at harvest adjusted to 15.5% moisture.

Moisture. The actual percentage moisture of the grain at harvest.

GDU Silk. The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are:

$$GDU = \frac{(Max.+Min)}{2} - 50.$$

The highest maximum used is 86° F. and the lowest minimum used is 50° F. For each hybrid, it takes a certain number of GDUs to reach various stages of plant development. GDUs are a way of measuring plant maturity.

Stalk Lodging. The percentage of plants that stalk lodge, i.e., stalk breakage, as measured by natural lodging or by pushing the stalks to determine the percentage of plants that break off below the ear. This is a relative rating of a hybrid to other hybrids for standability.

Root Lodging. The percentage of plants that root lodge; i.e., those that lean from the vertical axis at an approximate 30° angle or greater.

Plant Height. This is a measure of the height of the hybrid from the ground to the tip of the tassel, and is measured in centimeters.

Ear Height. The ear height is a measure from the ground to the ear node attachment, and is measured in centimeters.

Dropped Ears. The percentage of plants that dropped an ear prior to harvest.

Allele. The allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Essentially all the physiological and morphological characteristics. A plant having essentially all the physiological and morphological characteristics means a plant having the physiological and morphological characteristics, except for the characteristics derived from the converted gene.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

DETAILED DESCRIPTION OF THE INVENTION

GSC3 is a yellow dent corn inbred line with superior characteristics, and provides an excellent parental line in crosses for producing first generation ($F_1$) hybrid corn.

GSC3 is a corn inbred line developed by making a diallel cross of four proprietary inbred lines (329, 316, 317 and 335) and subsequently sibbing and selfing from the resultant population. Yield, stalk quality, root quality, disease tolerance, late plant greenness, late plant intactness, ear retention, pollen shedding ability, silking ability and corn borer tolerance were the criteria used to determine the rows from which ears were selected.

Inbred corn line GSC3 has the following morphologic and other characteristics (based primarily on data collected at Platteville, Wis.).

VARIETY DESCRIPTION INFORMATION

1. TYPE: Yellow Dent
2. REGION WHERE DEVELOPED: Northcentral U.S.
3. MATURITY:

|  | Days | Heat Units |
| --- | --- | --- |
| From emergence to 50% of plants in silk: | 71 | 1154 |
| From emergence to 50% of plants in pollen | 73 | 1197 |

$$\text{Heat Units} := \frac{[\text{Max. Temp. } (\leq 86° \text{F.}) + \text{Min. Temp. } (\geq 50°\text{F.})]}{2} - 50$$

4. PLANT:
   Plant Height (to tassel tip): 213.1 cm
   Ear Height (to base of top ear): 62.7 cm
   Average Length of Top Ear Internode: 15.9 cm
   Average Number of Tillers: 0
   Average Number of Ears per Stalk: 2
   Anthocyanin of Brace Roots: Moderate
5. LEAF:
   Width of Ear Node Leaf: 8.7 cm
   Length of Ear Node Leaf: 76.0 cm
   Number of Leaves Above Top Ear: 6
   Leaf Angle from 2nd Leaf Above Ear at Anthesis to Stalk Above Leaf: 21°
   Leaf Color: Very dark green (7.5GY ¾ Munsell)
   Leaf Sheath Pubescence (rate on a scale from 1=none to 9=like peach fuzz): 9
   Marginal Waves (rate on a scale from 1=none to 9=many): 3
6. TASSEL:
   Number of Lateral Branches: 3
   Branch Angle from Central Spike: 19°
   Tassel Length (from top leaf collar to tassel top): 39.8 cm
7a. EAR (Unhusked Data):
   Silk Color (3 days after emergence): Light Green (2.5GY 8/2 Munsell)
   Fresh Husk Color (25 days after 50% silking): Medium-green (5GY %  Munsell)
7b. EAR (Husked Data):
   Ear Length: 17.4 cm
   Ear Diameter at Mid-point: 36.4 mm
   Ear Weight: 120.5 g
   Number of Kernel Rows: 14
   Kernel Rows: Indistinct
   Row Alignment: Slightly curved
   Ear Taper: Slight
8. KERNEL (Dried):
   Kernel Length: 8.9 mm
   Kernel Width: 6.8 mm
   Kernel Thickness: 4.4 mm
   Weight per 100 Kernels (unsized sample): 24.9 g
9. COB:
   Cob Diameter at Mid-point: 24.9 mm
   Cob Color: Salmon (10R 4/10 Munsell)

This invention is also directed to methods for producing a corn plant by crossing a first parent corn plant with a second parent corn plant, wherein the first or second corn plant is the inbred corn plant from the line GSC3. Further, both first and second parent corn plants may be from the inbred line GSC3. Therefore, any methods using the inbred corn line GSC3 are part of this invention: selfing, backcrosses, hybrid breeding, and crosses to populations. Any plants produced using inbred corn line GSC3 as a parent are within the scope of this invention. Advantageously, the inbred corn line is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

The present invention contemplates a corn plant regenerated from a tissue culture of an inbred (e.g., GSC3) or hybrid plant of the present invention. As is well known in the art, tissue culture of corn can be used for the in vitro regeneration of a corn plant. By way of example, a process of tissue culturing and regeneration of corn is described in European Patent Application, publication 160,390, the disclosure of which is incorporated by reference. Corn tissue culture procedures are also described in Green & Rhodes (I 982) and Duncan, et al., (1985). The study by Duncan et al., (1985) indicates that 97 percent of cultured plants produced calli capable of regenerating plants. Subsequent studies have shown that both inbreds and hybrids produced 91 percent regenerable calli that produced plants.

Other studies indicate that non-traditional tissues are capable of producing somatic embryogenesis and plant regeneration. See, e.g., Songstad et al., (1988); Rao et al., (1986); and Conger et al., (1987), the disclosures of which are incorporated herein by reference. Regenerable cultures may be initiated from immature embryos as described in PCT publication WO 95/06128, the disclosure of which is incorporated herein by reference.

Thus, another aspect of this invention is to provide for cells which upon growth and differentiation produce the inbred line GSC3.

Proprietary inbred lines 329, 316, 317 and 335 are progenitors of GSC3 and property of Golden Seed Company, L.L.C. of Cordova, Ill. GSC3 is considerably different in plant height and appearance than its four progenitors. It also has a more narrow type ear with more round flinty type kernels than any of its progenitors.

Some of the criteria used to select plants within various generations include: yield, stalk quality, root quality, disease tolerance, late plant greenness, late season plant intactness, ear retention, pollen shedding ability, silking ability, and corn borer tolerance. During the development of the GSC3 line, crosses were made to inbred testers for the purpose of estimating the line's general and specific combining ability, and evaluations were run by the Platteville, Wis. Research Station. The inbred was evaluated further as a line and in numerous crosses by research stations across the Corn Belt including Platteville, Wis. The inbred proved to have a very good combining ability in hybrid combinations.

The inbred has shown uniformity and stability. It has been self-pollinated and ear-rowed for a sufficient number of generations, with careful attention to uniformity of plant type to ensure homozygosity and phenotypic stability. The line has been increased both by hand and sibbed in isolated fields with continued observations for uniformity. No variant traits have been observed or are expected in GSC3.

TABLES

In the tables that follow, the traits and characteristics of inbred corn line GSC3 are given in hybrid combination. The data collected on inbred corn line GSC3 is presented for the key characteristics and traits. The tables present yield test information about GSC3. GSC3 was tested in one hybrid combination at numerous locations, with two or three replications per location. Information about this hybrid combination, as compared to several widely sold competitive hybrids, is presented.

In the following tables, information for each hybrid includes:

1. The hybrids tested are listed in column 1.
2. The mean yield of the hybrid across all locations is in column 2.
3. The mean for the percentage moisture (% MO) for the hybrid across all locations is in column 3.
4. The mean of the percentage of plants with stalk lodging (% SL) across all locations is in column 4.
5. The mean of the percentage of plants with root lodging (% RL) across all locations is in column 5.
6. The mean of the percentage of plants with dropped ears (% DE) across all locations is in column 6.

TABLE 1

1997 Summary

| Hybrid | Yield | % MO | % SL | % RL | % DE |
|---|---|---|---|---|---|
| GSC3 × 354 | 154.7 | 23.4 | 3.9 | 6.4 | 0.0 |
| Pioneer Brand 3751 | 148.5 | 23.9 | 5.6 | 0.8 | 0.1 |
| CV | 10.0 | 5.8 | 101.4 | 206.1 | 523.8 |
| LSD | 10.0 | 1.0 | 2.2 | 3.6 | 0.2 |
| REPS | 12 | 12 | 12 | 12 | 12 |

TABLE 2

1996 Summary

| Hybrid | Yield | % MO | % SL | % RL | % DE |
|---|---|---|---|---|---|
| GSC3 × 402 | 157.2 | 20.3 | 5.2 | 7.2 | 1.8 |
| Pioneer Brand 3893 | 149.8 | 19.7 | 6.2 | 5.0 | 0.2 |
| Pioneer Brand 3905 | 146.3 | 18.8 | 4.2 | 4.7 | 0.1 |
| Pioneer Brand 3921 | 136.8 | 19.7 | 3.9 | 5.9 | 0.2 |
| CV | 9.4 | 3.6 | 91.6 | 152.0 | 295.0 |
| LSD | 6.6 | 0.4 | 1.6 | 5.4 | 0.7 |
| REPS | 60 | 60 | 55 | 33 | 26 |

When the term inbred corn plant is used in the context of the present invention, this also includes any single gene conversions of that inbred. The term single gene converted plant as used herein refers to those corn plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Poehiman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. No. 5,777,196, the disclosure of which is specifically hereby incorporated by reference.

A further aspect of the invention relates to tissue culture of corn plants designated GSC3. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, kernels, ears, cobs, leaves, husks, stalks, roots, root tips, anthers, silk and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as tassels or anthers, has been used to produce regenerated plants. (See U.S. Pat. No. 5,445,961 and U.S. Pat. No. 5,322,789, the disclosures of which are incorporated herein by reference).

DEPOSIT INFORMATION

A deposit of the Golden Seed Company inbred corn line GSC3 disclosed above and recited in the appended claims has been made with the American Type Culture Collection (ATCC), 10801 University Boulevard, Manassas, Va. 20110. The date of deposit was Aug. 16, 2000. The deposit of 2,500 seeds were taken from the same deposit maintained by Golden Seed Company since prior to the filing date of this application. All restrictions upon the deposit have been removed, and the deposit is intended to meet all the requirements of 37 C.F.R. §1.801-1.809. The ATCC accession number is PTA-2375. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn seed designated GSC3, wherein a sample of said seed has been deposited under ATCC Accession No. PTA-2375.

2. A corn plant, or its parts, produced by growing the seed of claim 1.

3. Pollen of the plant of claim 2.

4. An ovule of the plant of claim 2.

5. A corn plant having all of the physiological and morphological characteristics of the corn plant of claim 2, or its parts.

6. Tissue culture of the seed of claim 1.

7. A corn plant regenerated from the tissue culture of claim 6, wherein said corn plant is capable of expressing all the physiological and morphological characteristics of inbred corn line GSC3.

8. Tissue culture of regenerable cells of the plant, or its parts, of claim 2.

9. The tissue culture of claim 8, wherein the regenerable cells are embryos, meristematic cells, pollen, leaves, anthers, roots, root tips, silk, flower, kernels, ears, cobs, husks, stalks, or protoplasts or calli derived therefrom.

10. A corn plant regenerated from the tissue culture of claim 9.

11. A method for producing a hybrid corn seed comprising crossing a first inbred parent corn plant with a second inbred parent corn plant and harvesting the resultant hybrid corn seed, wherein said first or second parent corn plant is the corn plant of claim 2.

12. A hybrid corn seed produced by the method of claim 11.

13. A hybrid corn plant, or its parts, produced by growing said hybrid corn seed of claim 12.

14. Corn seed produced by growing said hybrid corn plant of claim 13.

15. A corn plant, or its parts, produced from seed of claim 14.

16. A method for producing a hybrid corn seed comprising crossing an inbred plant according to claim 2 with another, different corn plant.

17. A hybrid corn seed produced by the method of claim 16.

18. A hybrid corn plant, or its parts, produced by growing said hybrid corn seed of claim 17.

19. Corn seed produced from said hybrid corn plant of claim 18.

20. A corn plant, or its parts, produced from the corn seed of claim 19.

21. The corn plant of claim 5, further comprising a single gene conversion.

22. The corn plant of claim 21, further comprising a cytoplasmic factor conferring male sterility.

23. The single gene conversion of the corn plant of claim 21, where the gene is a transgenic gene.

24. The single gene conversion of the corn plant of claim 21, where the gene is a dominant allele.

25. The single gene conversion of the corn plant of claim 21, wherein the gene is a recessive allele.

26. The single gene conversion corn plant of claim 21, where the gene confers herbicide resistance.

27. The single gene conversion of the corn plant of claim 21, where the gene confers insect resistance.

28. The single gene conversion of the corn plant of claim 21, where the gene confers resistance to bacterial, fungal, or viral disease.

29. The single gene conversion of the corn plant of claim 21, where the gene confers male sterility.

30. The single gene conversion of the corn plant of claim 21, where the gene confers waxy starch.

* * * * *